(12) United States Patent
Schugt et al.

(10) Patent No.: US 8,939,905 B2
(45) Date of Patent: Jan. 27, 2015

(54) ANTENNA STRUCTURES FOR IMPLANTABLE MEDICAL DEVICES

(75) Inventors: Michael A. Schugt, St. Paul, MN (US); Yanzhu Zhao, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 462 days.

(21) Appl. No.: 13/250,755

(22) Filed: Sep. 30, 2011

(65) Prior Publication Data

US 2013/0085350 A1 Apr. 4, 2013

(51) Int. Cl.
| | |
|---|---|
| *A61B 5/07* | (2006.01) |
| *A61B 5/0215* | (2006.01) |
| *A61N 1/372* | (2006.01) |
| *A61B 5/00* | (2006.01) |
| *A61N 1/375* | (2006.01) |

(52) U.S. Cl.
CPC ............ *A61N 1/37229* (2013.01); *A61B 5/686* (2013.01); *A61N 1/3754* (2013.01); *A61B 5/0031* (2013.01); *A61B 5/0215* (2013.01); *A61B 5/6876* (2013.01); *A61N 1/3756* (2013.01); *A61N 1/37205* (2013.01)
USPC ........... 600/302; 600/481; 600/485; 600/505; 607/60

(58) Field of Classification Search
USPC ................................ 600/302; 607/32, 36, 60
See application file for complete search history.

(56) References Cited

U.S. PATENT DOCUMENTS

| | | |
|---|---|---|
| 5,861,019 A | 1/1999 | Sun et al. |
| 6,053,873 A | 4/2000 | Govari |
| 6,115,634 A | 9/2000 | Donders et al. |

(Continued)

FOREIGN PATENT DOCUMENTS

| | | |
|---|---|---|
| WO | 2004039450 A1 | 5/2004 |
| WO | 2007136657 A2 | 11/2007 |
| WO | 2009082286 A1 | 7/2009 |

OTHER PUBLICATIONS

"Feed Line." Nov. 6, 2006. http://searchmobilecomputing.techtarget.com/definition/feed-line.*

(Continued)

*Primary Examiner* — Navin Natnithithadha
*Assistant Examiner* — Meredith Weare
(74) *Attorney, Agent, or Firm* — Michael J. Ostrom; Stephen W. Bauer

(57) ABSTRACT

This disclosure describes antenna structures for use with implantable medical devices (IMDs). The IMD may include a housing that hermetically encloses electronic components of the IMD and a fixation mechanism that attaches the IMD to a target location within a patient, such as a wall of a vessel. The fixation mechanism may function as a radiating element of an antenna of the IMD. The fixation mechanism may be attached to a housing of the IMD with two different members. One member may be an anchoring structure that mechanically anchors the fixation mechanism to the housing. The second member may be a connector that electrically connects the fixation mechanism to the housing such that the fixation mechanism is configured to transmit and/or receive communication signals with other implantable or external devices.

26 Claims, 9 Drawing Sheets

(56) References Cited

U.S. PATENT DOCUMENTS

| | | | |
|---|---|---|---|
| 7,047,076 B1* | 5/2006 | Li et al. | 607/36 |
| 7,317,946 B2 | 1/2008 | Twetan et al. | |
| 7,363,087 B2 | 4/2008 | Ngheim et al. | |
| 7,452,334 B2* | 11/2008 | Gianchandani et al. | 600/485 |
| 7,613,522 B2 | 11/2009 | Christman et al. | |
| 7,903,043 B2 | 3/2011 | Rawat et al. | |
| 7,922,667 B2* | 4/2011 | Gianchandani et al. | 600/505 |
| 8,412,352 B2* | 4/2013 | Griswold et al. | 607/126 |
| 2003/0114735 A1* | 6/2003 | Silver et al. | 600/300 |
| 2005/0043765 A1 | 2/2005 | Williams | |
| 2005/0080346 A1* | 4/2005 | Gianchandani et al. | 600/486 |
| 2005/0273014 A1* | 12/2005 | Gianchandani et al. | 600/505 |
| 2006/0089682 A1 | 4/2006 | Kronich | |
| 2009/0254138 A1* | 10/2009 | Stahmann | 607/6 |
| 2009/0281401 A1 | 11/2009 | Takenaka et al. | |
| 2010/0022894 A1* | 1/2010 | Tittelbach et al. | 600/481 |
| 2010/0082080 A1 | 4/2010 | Mateychuk | |
| 2010/0109966 A1* | 5/2010 | Mateychuk et al. | 343/841 |
| 2010/0179449 A1* | 7/2010 | Chow et al. | 600/561 |
| 2011/0160557 A1 | 6/2011 | Cinbis | |
| 2012/0029323 A1* | 2/2012 | Zhao | 600/302 |
| 2012/0109002 A1* | 5/2012 | Mothilal et al. | 600/549 |

OTHER PUBLICATIONS

Chow et al. "Evaluation of Cardiovascular Stents as Antennas for Implantable Wireless Applications." IEEE Transactions on Microwave Theory and Techniques, vol. 57, Issue 10, Oct. 2009, pp. 2523-2532.*

"PIFA—The Planar Inverted—F Antenna." Antenna Theory. Feb. 25, 2011. https://web.archive.org/web/20110225234003/http://www.antenna-theory.com/antennas/patches/pifa.php.*

(PCT/US2012/057514) PCT Notification of Transmittal of the International Search Report and the Written Opinion of the International Searching Authority, 10 pages.

Chow et al., "Evaluation of Cardiovascular Stents as Antennas for Implantable Wireless Applications," IEEE Transactions on Microwave Theory and Techniques, vol. 57, No. 10, pp. 2523-2532, Oct. 2009.

Chow et al., "High Frequency Transcutaneous Transmission using Stents Configured as a Dipole Radiator for Cardiovascular Implantable Devices," IMS 2009, pp. 1317-1320.

Irazoqui et al., "Intracardiac Devices for Continuous Heart Failure Monitoring," PowerPoint presentation from Purdue University, accessed Apr. 21, 2011, 26 pp.

* cited by examiner

ANTENNA STRUCTURES FOR IMPLANTABLE MEDICAL DEVICES

TECHNICAL FIELD

The disclosure relates generally to implantable medical devices and, in particular, to antenna structures for implantable medical devices.

BACKGROUND

A wide variety of implantable medical devices (IMDs) that sense one or more parameters of a patient, deliver a therapy to the patient, or both have been clinically implanted or proposed for clinical implantation in patients. An IMD may deliver therapy to, and/or monitor a physiological condition with respect to, a variety of organs, nerves, muscles, tissues or vasculatures of the patient, such as the heart, brain, stomach, spinal cord, pelvic floor, or the like. The therapy provided by the IMD may include electrical stimulation therapy, drug delivery therapy or the like.

The IMD may transmit communications to and/or receive communications from another device via wireless telemetry. The IMD may transmit and/or receive communications with another device that is implanted, attached to (e.g., worn by) the patient or otherwise located near the patient, or remote from the patient. The communications may include information related to a condition of the patient, such as physiological signals measured by one or more sensors, information related to a therapy delivered to the patient, or information that may be used to control or configure a therapy to be delivered to the patient. The IMD may transmit and/or receive information using any of a variety of wireless communication techniques, including inductive telemetry, magnetic telemetry, radio frequency (RF) telemetry or the like.

SUMMARY

This disclosure describes antenna structures for an implantable medical device (IMD) for wirelessly communicating with another device. The IMD may include a housing that hermetically encloses electronic components of the IMD and a fixation mechanism that fixes the IMD relative to a target location within a patient, such as a wall of a cavity or body lumen. The fixation mechanism may function as a radiating and receiving element of an antenna of the IMD.

In one example, the disclosure is directed to an implantable medical device that includes an implantable housing including a telemetry module, a fixation mechanism mechanically anchored to the housing, and a connector electrically connecting the fixation mechanism to the telemetry module, wherein the fixation mechanism is configured to operate as at least a portion of an antenna to at least one of transmit or receive communication signals.

In another example, the disclosure is directed to a system that includes a device configured to be implanted within a patient, a fixation mechanism configured to be implanted within the patient, an anchoring structure configured to mechanically anchor the fixation mechanism to the device, and a connector configured to electrically couple the fixation mechanism to telemetry circuitry within the device.

In a further example, this disclosure is directed to a device that includes an implantable housing comprising a telemetry module, means for attaching the housing to an anatomical structure within a patient, wherein the attaching means is mechanically anchored to the housing, and means for electrically connecting the attaching means to the telemetry module, wherein the attaching means is configured to operate as at least a portion of an antenna to at least one of transmit or receive communication signals.

The details of one or more examples are set forth in the accompanying drawings and the description below. Other features, objects, and advantages will be apparent from the description and drawings, and from the claims.

DETAILED DESCRIPTION

Figure 1:
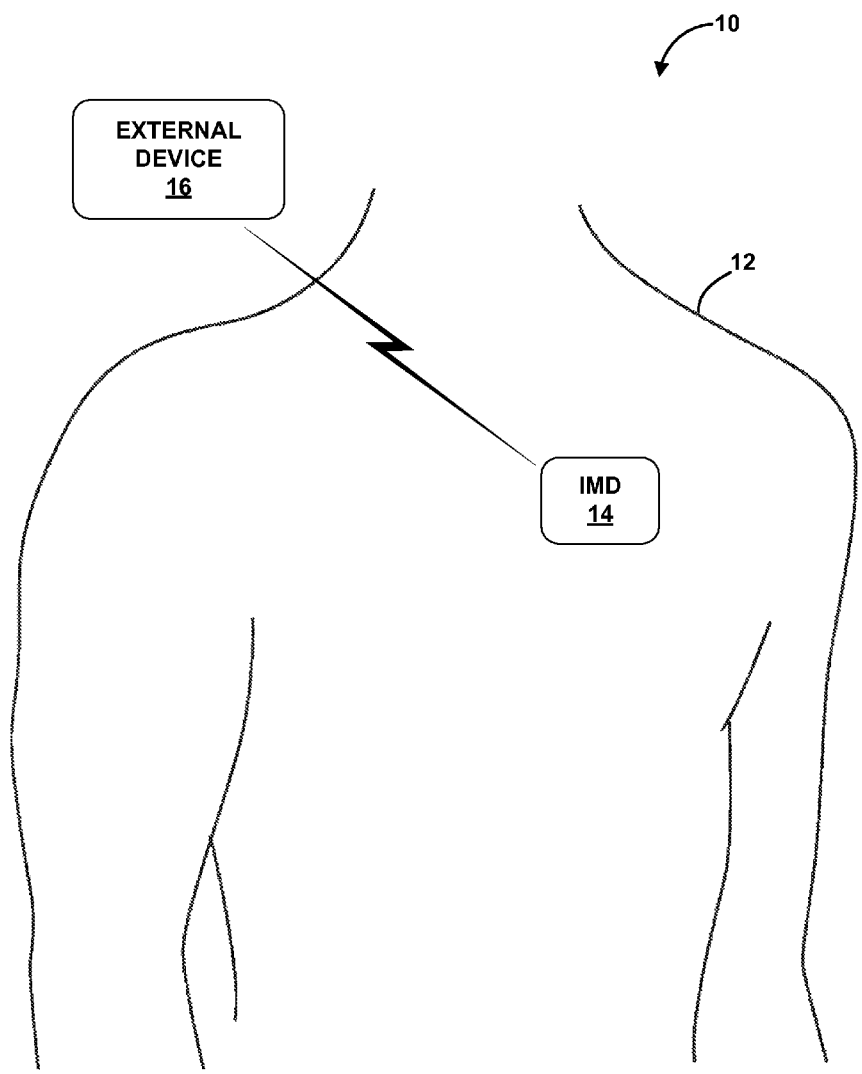
FIG. 1 is a conceptual diagram illustrating an example system that includes an external device and an IMD.

As described herein, an implantable medical device (IMD) may include an antenna structure for wirelessly communicating with another device. The antenna structure may take the form of a fixation mechanism used to affix, attach, or otherwise position the IMD relative to a tissue site within a patient. Although IMDs of smaller dimensions may allow the IMD to be implanted within a patient at locations not possible with larger devices, wireless telemetry using an antenna within or disposed on these smaller IMDs may have limited effectiveness. Generally, reducing the size of an antenna may reduce the efficiency of the antenna and/or reduce the range of wireless telemetry. However, a fixation mechanism disposed external of the IMD housing may be utilized as an antenna with larger dimensions than are otherwise possible within the IMD housing. The fixation mechanism may thus provide an antenna that is efficient and capable of wireless telemetry over larger distances than a smaller antenna limited to the size of the IMD housing.

In some cases, the fixation mechanism may be physically connected to the housing of the IMD with a member or connector (e.g., a feed-through) that electrically couples the fixation mechanism to telemetry circuitry within the IMD housing. The connector may be constructed with materials and/or dimensions selected to facilitate sufficient electrical coupling between the housing and the fixation mechanism. However, this connector may not be sufficient to provide a mechanical anchor or structural connection between the fixation mechanism and the housing. Forces created by pressure within a tissue site may produce mechanical strain. In the pulmonary artery, for example, bending of surrounding tissues that contact the fixation mechanism and/or the housing, or other environmental factors surrounding the fixation mechanism and the housing, may put mechanical strain and stress at the electrical connection. This stress and strain may compromise the structural integrity of the electrical connection when the connection is also used to mechanically anchor the fixation mechanism to the IMD housing.

In accordance with an example of this disclosure, a fixation mechanism may be connected to the IMD housing two or more members. One of these members may be the electrical connector (e.g., a feed-through connector) used by the IMD to employ the fixation mechanism as a part of an antenna. In this manner, the fixation mechanism may be used to transmit and/or receive communication signals, i.e., to or from other implantable or external devices. A different member may then be an anchoring structure that mechanically anchors the fixation mechanism to the IMD housing. The anchoring structure may provide added structural integrity and durability to the physical connection between the fixation mechanism and the IMD housing. In particular, the anchoring structure may act as a mechanical support that resists physical separation of the fixation mechanism from the IMD housing. Consequently, the electrical connector may be exposed to reduce mechanical stress and strain from the fixation mechanism. The electrical connector may thus provide an electrical connection between the fixation mechanism of the antenna and the IMD circuitry and may be constructed of dimensions and materials selected for optimal electrical performance as a primary consideration, e.g., with less concern for structural integrity in the presence of external forces. In one example, the electrical connector may also be at least partially deformable to reduce any strain on the connector that may be caused by movement between the fixation mechanism and the housing.

Figure 4:
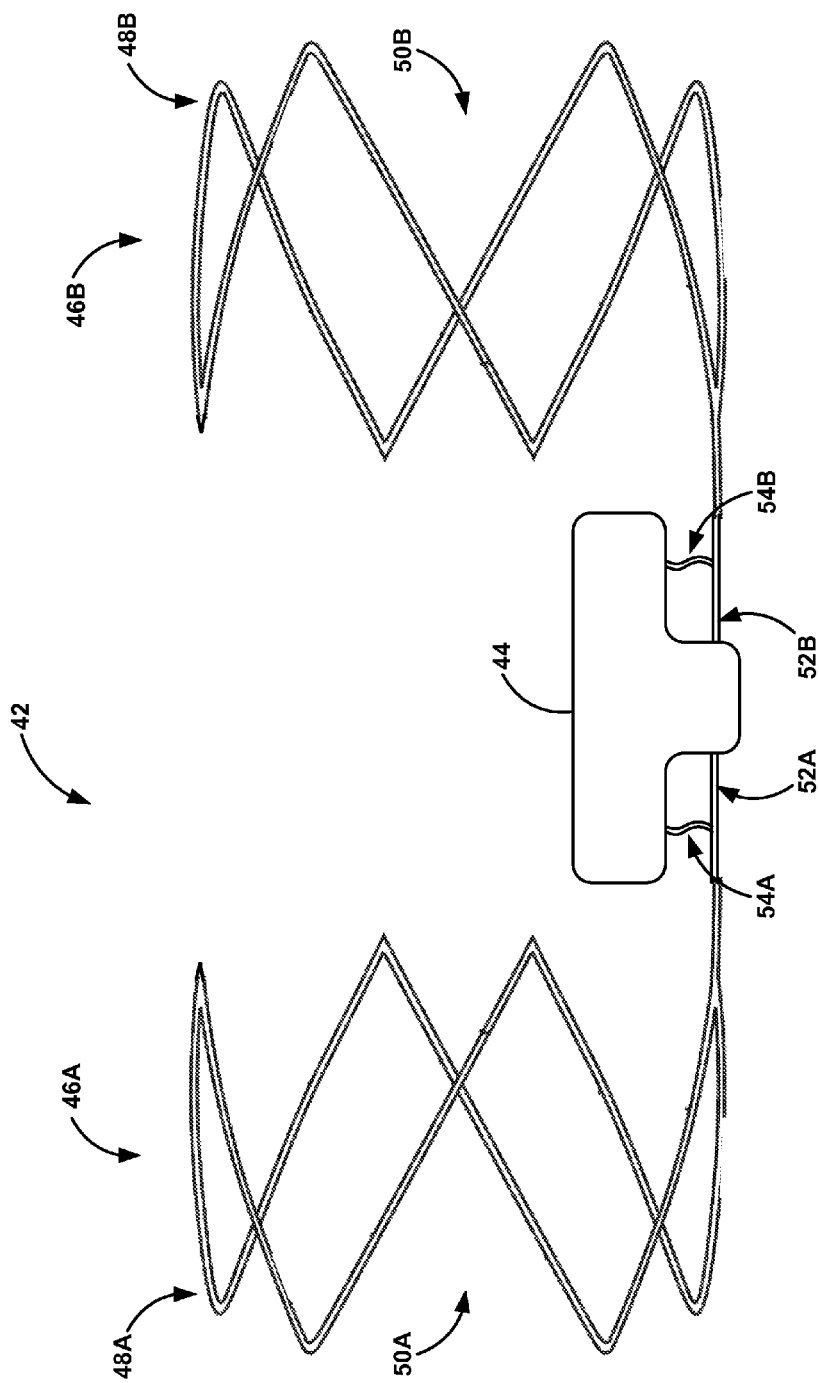
FIG. 4 is a conceptual diagram illustrating an IMD with two fixation mechanisms that function as radiating and/or receiving elements of an antenna.

In some examples, the anchoring structure may be an extension of or formed as a part of the fixation mechanism. The anchoring structure may also act as an electrical ground to the IMD housing. This electrical ground, or shorting member, may allow the antenna to be resonant at wavelengths other than the wavelength of the transmitted signal (e.g., a planar inverted F-antenna that is resonant at quarter-wavelength of the transmission signal). However, any electrical signal transmitted from the IMD or received by the fixation mechanism antenna may be transferred through the electrical connector. Although a single connector and a single anchoring structure may be sufficient for the IMD to operate, other examples may include two or more electrical connectors and/or two or more anchoring structures for a given fixation mechanism. In an example of two or more electrical connectors, one of these electrical connectors may be used to ground the fixation mechanism to the IMD housing. In addition, multiple electrical connectors may be utilized with multiple fixation mechanisms as shown in FIG. 4.

The fixation mechanism may be any structure configured to position the housing to a target location within the patient. In positioning the housing, fixation mechanism may be positioned by interfacing with a portion of tissue. For example, the fixation mechanism may be secured to the tissue through friction, deformation of the tissue (e.g., indentation of the tissue under pressure), tissue growth, clamping, piercing, adhesion, or any combination thereof. In some examples, the fixation mechanism may be a stent-like structure implanted within a vessel. The fixation mechanism may be configured to position the IMD housing to a desired anatomical structure, and, in some examples, the fixation structure may provide a therapeutic benefit to the patient (e.g., a stent-like structure may open and/or maintain patency of a lumen, such as an artery). In other examples, the fixation mechanism may include one or more elements that force against or pierce tissue surrounding the IMD (e.g., tines, needles, hooks, springs, or coils.

In one example, the IMD may be an implantable sensor for continuously monitoring a pressure within a vessel of the patient. However, the techniques described in this disclosure are applicable to any IMD that measures any of a variety of parameters of the patient, provides a therapy to the patient, or both.

FIG. 1 is a conceptual diagram illustrating example system 10 that includes external device 16 and IMD 14. System 10 includes an implantable medical device (IMD) 14 and an external device 16. Medical system 10 may, however, include one or more implanted, body worn or external devices. IMD 14 and external device 16 may communicate with one another using any of a number of wireless communication techniques, including inductive telemetry, radio frequency (RF) telemetry or the like.

IMD 14 may be any of a variety of medical devices that sense one or more parameters of patient 12, provide therapy to patient 12, or a combination thereof. In one example, IMD 14 may be a leadless IMD. In this case, IMD 14 may be implanted at a targeted site with no electrical leads extending from the IMD into a target area of patient 12, thus avoiding limitations associated with lead-based devices. Instead, sensing and therapy delivery components may be self-contained within IMD 14. In other examples, IMD 14 may include one or more electrical leads.

In another example, IMD 14 may be a leadless sensor that includes one or more sensors that measure one or more parameter(s) of patient 12. In one example, IMD 14 may comprise an implantable pressure sensor placed within a vasculature or chamber of a heart of patient 12. Although this disclosure is described with respect to IMD 14 being an implantable pressure sensor implanted within the cardiac vasculature or heart of patient 12, for purposes of illustration, IMD 14 may alternatively be placed in other locations within patient 12, such as within or proximate to a spinal cord, brain, stomach, intestinal tract, or pelvic floor. In this manner, IMD 14 may be configured to sense, sample, and/or process any of a variety of parameters such as heart activity, muscle activity, brain electrical activity, intravascular pressure, blood pressure, blood flow, acceleration, displacement, motion, respiration, or blood/tissue chemistry, such as oxygen saturation, carbon dioxide, pH, protein levels, enzyme levels, another parameter, or any combination of parameters. IMD 14 may then transmit the sensed parameters to another device, such as external device 16, a body worn device (not shown), or another IMD (not shown in FIG. 1), which may in turn monitor a condition of patient 12 or provide therapy to patient 12 as a function of the sensed parameters. For example, IMD 14 may transmit the sensed patient parameter to a therapeutic medical device implanted at a different location than that of IMD 14.

IMD 14 may provide the therapy to patient 12. In some examples, IMD 14 may provide the therapy to patient 12 on an open loop basis, or on a closed loop basis, e.g., as a function of sensed parameters measured by a sensor of IMD 14 or received from another device, such as another IMD or a body worn device. As one example, IMD 14 may be a leadless cardiac IMD that provides electrical stimulation therapy (e.g., pacing, cardioversion, defibrillation, and/or cardiac resynchronization) to the heart of patient 12 via one or more electrodes as a function of sensed parameters associated with the heart. In yet a further example, IMD 14 may provide therapy to patient 12 that is not provided as a function of the sensed parameters, such as in the context of neurostimulation.

Although described above in the context of electrical stimulation therapy, IMD 14 may provide other therapies to patient 12, such as delivery of a drug or therapeutic agent to patient 12 to reduce or eliminate the condition of the patient and/or one or more symptoms of the condition of the patient, or provide no therapy at all.

External device 16 may be a programming device or monitoring device that allows a user, e.g., physician, clinician or technician, to transmit operational instructions to IMD 14, configure a therapy delivered by IMD 14, and/or retrieve data sensed by IMD 14. External device 16 may also receive commands from IMD 14 such that IMD 14 functions as a master device that controls another device implanted within patient 12. External device 16 may include a user interface that receives input from the user and/or displays data to the user, thus allowing the user to program the therapy delivered by IMD 14 or display data retrieved from IMD 14. External device 16 may be a dedicated hardware device with dedicated software for programming or otherwise communicating with IMD 14. Alternatively, external device 16 may be an off-the-shelf computing device executing an application that enables external device 16 to program or otherwise communicate with IMD 14. In one example, external device 16 may be a computer workstation, such as a Medtronic CareLink® monitor, available from Medtronic, Inc. of Minneapolis, Minn. In other examples, external device 16 may be another device that delivers therapy to patient 12.

In some instances, IMD 14 and external device 16 may be communicatively coupled with each other as well as other medical devices (not shown) to form a local area network, sometimes referred to as a body area network (BAN) or personal area network (PAN). Each device may therefore be enabled to communicate wirelessly along multiple pathways with each of the other networked devices. As such, IMD 14 and external device 16 may represent a distributed system of devices that cooperate to monitor a condition of and/or provide therapy to patient 12. Additionally, one or more of the devices may be coupled to a remote computing device via one or more wired or wireless networks, such as a local area network (LAN), wide area network (WAN), or global network, such as the Internet.

IMD 14 and external device 16 may communicate with one another by any of a number of wireless communication techniques. In some instances, IMD 14 may communicate with external device 16 via RF telemetry. RF telemetry provides communication at further distances than conventional inductive telemetry such that no telemetry head is needed in the case of RF telemetry. IMD 14 and/or external device 16 may communicate in accordance with the Medical Implant Communications Service (MICS) band regulation and/or the Medical External Data Service (MEDS) frequency band regulation. The MICS band regulation defines communication requirements for the 402-405 MHz frequency band. In accordance with the MICS band regulations, the frequency band is divided into ten channels with each channel corresponding to a 300 kilohertz (kHz) sub-band. The MEDS band regulation defines a split channel band with a portion of the MEDS band occupying the 401-402 MHz frequency band and a portion of the MEDS band occupying the 405-406 MHz frequency band. The MEDS band is divided into 20 channels with each channel corresponding to a 100 kHz sub-band, with the first ten channels being located in the 401-402 MHz frequency band and the second ten channels being located in the 405-406 MHz frequency band. The devices of system 10 may, however, communicate using any frequency band in addition to or instead of the MICS and MEDS band regulations, such as the industrial, scientific and medical (ISM) frequency bands.

As described herein, system 10 may include one or more devices in addition to IMD 14 that includes a fixation mechanism as a radiating portion of an antenna. This radiating portion of the antenna may function to transmit signals from IMD 14 and/or receive signals from another device. For example, external device 16 may be an external programmer configured to communicate with IMD 14 via the fixation mechanism. In addition, system 10 may include one or more implantable and/or body worn devices that each communicate with IMD 14. Since IMD 14 may include a fixation mechanism antenna capable of increased telemetry range, system 10 may utilize IMD 14 for relaying data between other devices and external device 16. In this manner, other implanted and/or body worn devices may only include telemetry circuitry capable of reaching IMD 14. Then, IMD 14 may provide increased distance telemetry to external device 16.

Figure 2:
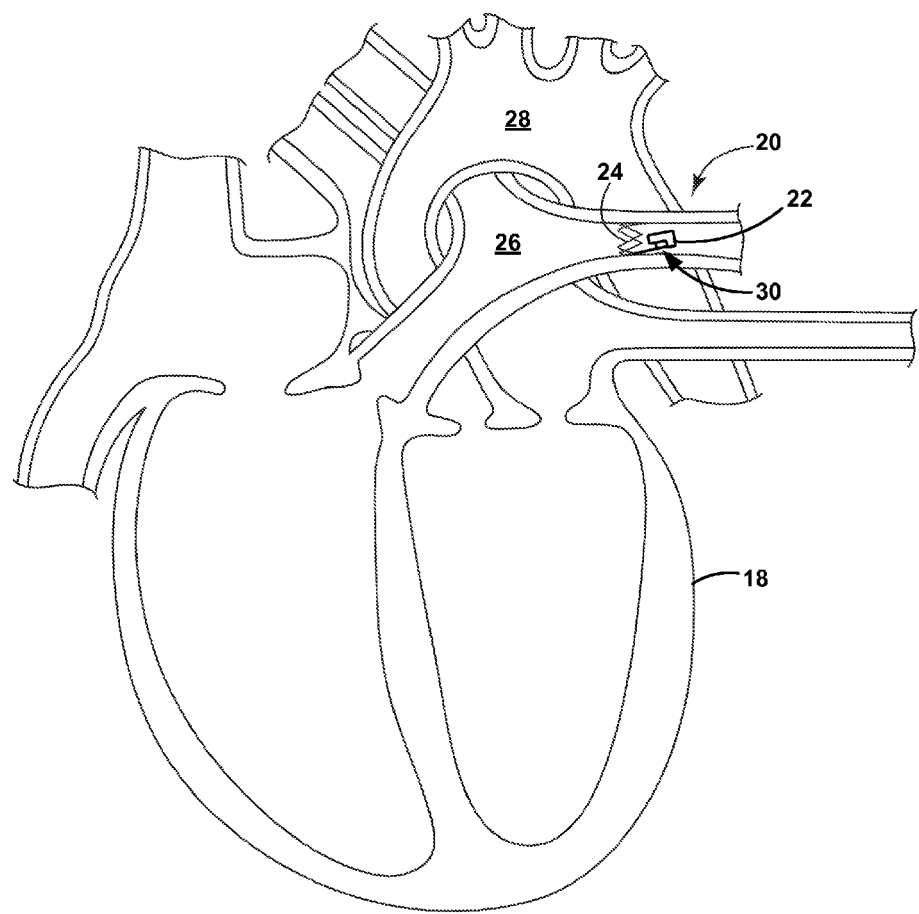
FIG. 2 is a conceptual diagram illustrating an example IMD implanted in a heart.

FIG. 2 is a conceptual diagram illustrating example IMD 20 implanted in pulmonary artery 26. In one example, IMD 20 may be an example of IMD 14 of FIG. 1. In another example, IMD 20 may communicate with IMD 14 of FIG. 1 within system 10. In the example illustrated in FIG. 2, IMD 20 is implanted in pulmonary artery (PA) 26 adjacent to heart 18. As such, IMD 20 may be sized to be delivered endoluminally using a delivery system tracked through the vasculature from a percutaneous entry site such as a femoral, jugular or subclavian vein or artery, and may have an outer diameter, for example, between 16 French and 18 French (approximately 5.3 to 6.0 mm). However, IMD 20 may be placed within other portions of the cardiovascular system, such as in one of the chambers (atrial or ventricular) of heart 18, veins, vessels, arteries or other vasculature (e.g., aorta 28, a renal artery, or inferior or superior vena cava). In further instances, IMD 20 may be placed on the outside of heart 18 or in locations other than the cardiovascular system.

IMD 20 includes a housing 22 coupled to a fixation mechanism 24. Housing 22 is illustrated in the example of FIG. 2 as a capsule-shaped housing that hermetically encloses components of IMD 20, such as at least one sensor, processor, memory, power source, telemetry circuitry, or the like. In one example, housing 22 may include a pressure sensing device that obtains pressure measurements in an environment surrounding housing 22. In this example, IMD 20 may be an active leadless pressure sensor system designed to monitor blood pressure (e.g., continuously or periodically) and transmit the pressure measurements to external device 18 of FIG. 1 to allow physicians to proactively administer medications so that patients avoid dangerous blood pressure spikes. However, IMD 20 may sense pressure measurements of other locations of the cardiovascular system depending on the location of implantation. In other examples, housing 22 may house sensor(s) for obtaining measurements of other parameters, such as heart activity, muscle activity, brain electrical activity, blood flow, acceleration, displacement, motion, respiration, or blood/tissue chemistry, such as oxygen saturation, carbon dioxide, pH, protein levels, enzyme levels or other parameter or combination of parameters.

Fixation mechanism 24 may position IMD 20 to the target location, such as the wall of pulmonary artery 26 in the example illustrated in FIG. 2. Fixation mechanism 24 of FIG. 2 may be a tubular or cylindrical stent-like structure that is configured to lodge against a vessel wall when implanted. A stent-like structure may include one or more struts, ribs, coils, mesh sections, or other members arranged in a tubular or cylindrical cage structure. In one example, fixation mechanism 24 is mechanically coupled to housing 22 such that IMD 20 is substantially radially centered within pulmonary artery 26 when implanted. In other example, fixation mechanism 24 may be mechanically coupled to housing 22 such that IMD 20 is adjacent to the wall of pulmonary artery 26 when implanted. Although illustrated as a stent-like fixation mechanism, fixation mechanism 24 may be a different fixation mechanism that exerts enough force against, embeds within, extends through or otherwise positions IMD 20 to the target location.

As will be described in further detail below, IMD 20 transmits and/or receives wireless signals via an antenna. In accordance with the techniques of this disclosure, fixation mechanism 24 functions as at least part of the antenna of IMD 20. Fixation mechanism 24 may, in one example, function as the radiating element of a plane inverted F-antenna and is electrically coupled to telemetry circuitry within IMD 20 via a feed line (e.g., an electrical connector). In addition to an electrical connector, a plane inverted F-antenna may utilize a ground or shorting pin that allows the impedance of the antenna to be selected for desired frequencies or otherwise tuned as needed. In other words, the ground provides inductance that can be used to optimize or tune the impedance of the antenna. When implanted, fixation mechanism 24 and housing 22 (e.g., a hermitic housing) may have a strong capacitive coupling due to high dielectric properties of the surrounding tissue. Therefore, the ground or shorting pin of may be used to tune or optimize the impedance of the IMD 20 antenna (e.g., fixation mechanism 24).

Since fixation mechanism 24 may be significantly larger in size than an antenna integrated within housing 22, using the fixation mechanism 24 as a radiating portion of the antenna may significantly improve overall radiation efficiency. This, in turn, may enable reduced power consumption and/or increased communication range with fixation mechanism 24 than would otherwise be possible with an integrated housing antenna.

By utilizing an anchoring structure 30 to mechanically anchor fixation mechanism 24 to housing 22, the electrical connector (e.g., a feed line) between fixation mechanism 24 and housing 22 may not be exposed to or exposed to reduced mechanical stresses and strains from movement of fixation mechanism 24 relative to housing 22. As described herein, housing 22 may include a telemetry module or telemetry circuitry for transmitting and/or receiving data. Fixation mechanism 24 may be mechanically anchored to housing 22, and a connector may electrically connect fixation mechanism 24 to the telemetry module. Therefore, fixation mechanism 24 may be configured to transmit and/or receive communication signals (e.g., fixation mechanism 24 may be a radiating element of an antenna for IMD 20.

Fixation mechanism 24 may include anchoring structure 30 configured to provide structural integrity between fixation mechanism 24 and housing 22. Even though anchoring structure 30 may be rigid or at least partially flexible, anchoring structure 30 may be resistant to fatigue and fracture from stress and strain. In this manner, anchoring structure 30 may be formed of or be a portion of fixation mechanism 24. In other examples, anchoring structure 30 may be a separate member that mechanically couples fixation mechanism 24 to housing 22. A separate anchoring structure 30 may include a receptacle that accepts a portion of fixation mechanism 24 and/or a clamp that couples anchoring structure 30 to housing 22. In this manner, a length, size, or shape of anchoring structure 30 may be selected for any different fixation mechanisms 24.

Anchoring structure 30 may be configured to support any stress and strain between fixation mechanism 24 and housing 22. In one example, anchoring structure 30 may have a stiffness that substantially prevents any movement between fixation mechanism 24 and housing 22. In another example, anchoring structure 30 may provide some elastic deformation such that fixation mechanism 24 may bend and/or twist with respect to housing 22. This elastic deformation of anchoring structure 30 may reduce the likelihood of failure of anchoring structure 30 after numerous pressure cycles within the vasculature.

Anchoring structure 30 may also be configured to electrically ground fixation mechanism 24 to housing 22. Anchoring structure 30 may contact housing 22 at one or more locations, and anchoring structure 30 may electrically ground fixation mechanism 24 at at least one of the contact locations with housing 22. In other examples, IMD 20 may include a separate ground connector that grounds fixation mechanism 24 to housing 22. This separate ground connector may not provide structural support between fixation mechanism 24 and housing 22.

Since anchoring structure 30 provides structural support for fixation mechanism 24, the electrical connector may not need to provide any structural support between fixation mechanism 24 and housing 22. In fact, it may be beneficial for the connector to include a deformable member connected to fixation mechanism 24 and configured to allow fixation mechanism 24 to move with respect to housing 22. This deformable member may be flexible in at least one plane and/or formed to reduce any stress or strain on the connector. In one example, the deformable member may be a ribbon connector with excess length to accommodate changing distances between fixation mechanism 24 and housing 22 within patient 12. In another example, the deformable member may be a coil that expands and contracts as needed to prevent fracture of the connector under stress or strain. Although the ribbon connector may be located entirely outside of housing 22, the ribbon connector (or any electrical connector) may be deformable within housing 22 to reduce stress and strain to the connector.

The deformable member, in some examples, may be the entire connector. The deformable member may contact fixation mechanism 24, feed through housing 22, and contact telemetry circuitry. In other examples, the connector may include a feed-through pin that electrically couples the deformable member to the telemetry module within housing 22. The feed-through pin may be electrically isolated from housing 22 and allow the deformable member to be disposed entirely outside of housing 22.

Fixation mechanism 24 may be mechanically anchored to housing 22 at one location or at at least two locations. Once anchoring location on housing 22 may be sufficient to attach fixation mechanism 24 and provide an adequate radiating structure in fixation mechanism 24. However, IMD 20 may include multiple anchoring locations for fixation mechanism 24 to provide durability and reduce the stress and strain on each anchoring location.

IMD 20 may include various components that allow IMD 20 to perform a variety of functions. For example, IMD 20 may include a sensor within housing 22 such that the sensor is configured to measure one or more parameters of patient 12. For example, the sensor within housing 22 may include one or more of a pressure sensor, a pH sensor, an oxygen sensor, a temperature sensor, and an electrode. A portion of the sensor may be disposed on housing 22 or otherwise external of housing 22 in order to measure the parameter of patient 12. IMD 20 may additionally, or alternatively, include a therapy module that generates and delivers therapy to patient 12. The therapy may include drug delivery therapy and/or electrical stimulation therapy.

Figure 3:
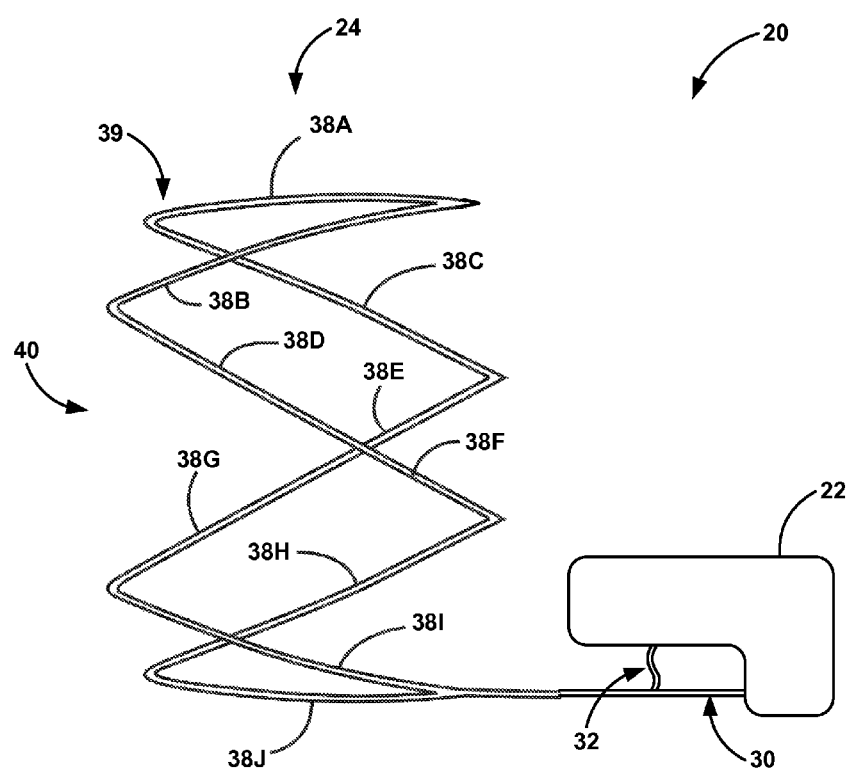
FIG. 3 is a conceptual diagram illustrating the IMD of FIG. 2 in further detail.

FIG. 3 is a schematic diagram illustrating an example of IMD 20 in further detail. As described above, housing 22 hermetically encloses components of IMD 20, such as at least a portion of a sensor, processor, memory, power supply, telemetry circuitry, or the like. In the example of FIG. 3, housing 22 has an "L" block shape to facilitate anchoring fixation mechanism 24. In other examples, housing 22 may be configured in a long, thin cylindrical shape (e.g., capsule-like shape) to reduce blood flow turbulence when implanted in pulmonary artery 26 (as illustrated in FIG. 2). Housing 22 may have other shapes depending on the location desired for implantation, shape of the fixation mechanism, type of sensor, or the like. For example, housing 22 may be formed in a different shape to accommodate placement within a chamber of heart 18, along a spine, in a brain, gastrointestinal tract or other location within or on patient 12. Therefore, the techniques described in this disclosure should not be limited by the shape of housing 22 described herein.

Housing 22 may be formed of any of a variety of materials including conductive materials, non-conductive materials, or a combination thereof. Examples of a biocompatible, conductive material includes titanium, stainless steel, MP35N® alloy (a nonmagnetic, nickel-cobalt-chromium-molybdenum alloy), or platinum or the like. Examples of a biocompatible, non-conductive materials include silicone rubber, polyurethane, epoxy, acetyl co-polymer plastics, PolyEtherEtherKetone (PEEK), liquid crystal polymer (LCP) plastics, or the like.

Housing 22 may be formed to have an opening that exposes a pressure sensing device to the environment at the target location. In other examples, housing 22 may be configured to allow IMD 20 to measure the appropriate parameters of patient 12. For example, housing 22 may include one or more electrodes to detect a pH of patient blood or an exposed thermocouple to measure the temperature of blood. Housing 22 may include other types of sensors instead of or in addition to a pressure sensing device, such as pH sensor, oxygen sensor, temperature sensor, electrode, or any other type of sensor. For example, housing 22 may include multiple electrodes for detecting an electrogram of surrounding electrical activity (e.g., cardiac muscle depolarizations).

Housing 22 is mechanically coupled to fixation mechanism 24 that positions IMD 20 to the target location within patient 12. Fixation mechanism 24 may be mechanically coupled to housing 22 via anchoring structure 30. In one example, anchoring structure 30 may be a member that is coupled to both fixation mechanism 24 and housing 22 via spot welding, an adhesive, crimping, a set screw, or other coupling mechanism. For example, anchoring structure 30 may be constructed of nitinol crimped or welded to housing 22 constructed of a titanium alloy. In other examples, anchoring structure 30 may be a portion of fixation mechanism 24 (e.g., anchoring structure 30 may be formed as a part of fixation mechanism 24). In this manner, anchoring structure 30 may be coupled to housing 22 via spot welding, an adhesive, one or more set screws, or other coupling mechanisms.

Telemetry circuitry within housing 22 may also be electrically coupled to fixation mechanism 24 using connector 32. Connector 32 may be physically coupled to fixation mechanism 24, housing 22, and telemetry circuitry (e.g., a telemetry module) contained within housing 22. Connector 32 may be a separate member that is crimped, welded, or otherwise adhered to fixation mechanism 24. Alternatively, connector 32 may be a portion of fixation mechanism 24. In other words, connector 32 and fixation mechanism 24 may be a one piece structure that is laser cut or otherwise formed with connector 32 protruding from fixation mechanism 24. Further, in other examples, fixation mechanism 24, anchoring structure 30, and connector 32 may be formed of a single structure. Connector 32 may be electrically isolated (e.g., using a feedthrough) from housing 22 where connector 32 enters housing 22. As described in more detail below, connector 32 may not provide any structural support for attaching fixation mechanism 24 to housing 22. Although connector 32 is shown as a curved member in FIG. 3 longer than the distance between housing 22 and fixation mechanism 24, connector 32 may be relatively straight in other examples as further described herein.

As described above, fixation mechanism 24 may be a generally tubular or cylindrical stent-like structure that is configured to lodge against a vessel wall when implanted to hold IMD 20 at the target location. In the example of FIG. 3, fixation mechanism 24 may include a plurality of struts 38A-38J that are arranged to form fixation mechanism 24. In particular, struts 38A-38J are arranged to form a ring 39 having a lumen 40. In the example illustrated in FIG. 3, struts 38A-38J form a zig-zag shaped ring 39. However, struts 38A-38J may be arranged to form a ring of a different shape, such as a sinusoidal shaped ring. Anchoring structure 30 mechanically anchors one end of ring 39 to housing 22 to attach fixation mechanism 24 to housing 22. In other examples, anchoring structure 30 may be an additional strut, similar to struts 38A-38J. Fixation mechanism 24 and anchoring structure 30 may be constructed such that ring 39 is any distance from housing 22. The distance between ring 39 and housing 22 may be selected to fit IMD 20 within a desired anatomical location or tune fixation mechanism 24 to a transmit and/or receive signals of a particular wavelength.

Fixation mechanism 24 may take on alternative configurations than that shown in FIG. 3. For example, a first portion of a plurality of struts may be configured to form a plurality of rings that are joined in series to form a cylindrical body. In other words, multiple rings 39 may be attached end-to-end to form a longer fixation mechanism with a longer lumen 40. At one end of the longer fixation mechanism, a second portion of the plurality of struts may be used to mechanically anchor the longer fixation mechanism to housing 22. Alternatively, a separate anchoring structure may be used to structurally anchor the longer fixation mechanism to housing 22.

Struts 38A-38J and anchoring structure 30 may be made from a variety of conductive materials suitable for implantation, including, but not limited to, nickel-titanium (nitinol), stainless steel, tantalum, nickel, titanium, nickel-cobalt-chromium-molybdenum "superalloy," combinations of the above, and the like. In some examples, a portion of struts 38A-38J and anchoring structure 30 may be made of one or more of the conductive materials described above while the other portions of struts 38A-38J and anchoring structure 30 may be made of non-conductive materials, such as polymeric materials. In this case, the conductive path of fixation mechanism 24 may be specifically designed to obtain a particular radiation pattern. Not only may non-conductive materials be used, but one or more portions of struts 38A-38J and anchoring structure 30 may be made of materials having various conductivities (e.g., resistance) to obtain a desired radiation pattern in fixation mechanism 24. The material from which struts 38A-38J and anchoring structure 30 are made may be capable of being manipulated such that fixation mechanism 24 may be radially compressed or otherwise manipulated to aid in delivery of IMD 20 to the target location. When located at the target location, fixation mechanism 24 may be expanded in situ, e.g., via inflation of a balloon, temperature expansion, or expansion to pre-formed state after compression from a sheath (not shown), such that at least a portion of struts 38 securely engage the vessel wall. In other examples, IMD 20 may include one or more tines, loops, or other mechanisms that may be used to position implantable sensor 20 to the target location. These other mechanisms may be provided in addition to fixation mechanism 24.

As described above with respect to FIG. 2, IMD 20 communicates with one or more other devices, such as external device 16 or another implantable medical device. To this end, IMD 20 includes fixation mechanism 24 for use as an antenna to transmit and receive signals from the one or more other devices. As described in detail herein, the antenna may include fixation mechanism 24, connector 32 to transfer excitation energy between fixation mechanism 24 and the telemetry module, and anchoring structure 30 to ground fixation mechanism 24 to housing 22.

The structure of IMD 20 illustrated in FIG. 3 provides a number of advantages. As one example, using fixation mechanism 24 as a radiating portion of the antenna may significantly improve overall radiation efficiency since fixation mechanism 24 is typically significantly larger in size than an integrated antenna within housing 22. This, in turn, enables reduced power consumption and/or a farther communication range by using fixation mechanism 24 instead of an antenna limited to the size of housing 22. As another example, anchoring structure 30 allows fixation mechanism 24 to be structurally connected to housing 22 without connector 32 needing to provide any structural support between housing 22 and fixation mechanism 24. In this manner, connector 32 may be constructed of a size and material most appropriate to excite fixation mechanism 24 as a radiating portion of the antenna of IMD 20. In other words, connector 32 may include a feed-through (not shown in FIG. 3) that does not function to structurally anchor fixation mechanism 24 to housing 22. Connector 32 is thus limited to any mechanical strain or stress generated by pressures and forces on fixation mechanism 24 that may compromise the electrical connection of connector 32. Additionally, the structure of fixation mechanism 24, connector 32, and anchoring structure 30 may be selected to match electrical impedances with the telemetry module, which may improve overall radiation efficiency.

The antenna structure illustrated in FIG. 3 (e.g. fixation mechanism 24, anchoring structure 30, and connector 32) is one example structure in accordance with this disclosure. However, the antenna structure of FIG. 3 should not be considered limiting of the techniques described herein. For instance, the techniques of this disclosure may be used with any fixation mechanism (e.g., ones having different mechanical structures) for which there is sufficient radiating area to be used as the radiating surface of an antenna. In addition, housing 22 may have alternative shapes that facilitate the connection to fixation mechanism 24 via anchoring structure 30 and connector 32.

FIG. 4 is a conceptual diagram illustrating IMD 42 with two fixation mechanisms 46A and 46B (collectively "fixation mechanisms 46) that function as radiating elements of an antenna. IMD 42 may be substantially similar to IMD 20 of FIG. 3. However, IMD 42 may include two or more fixation mechanisms 46. As shown in FIG. 4, IMD 42 includes housing 44 and fixation mechanisms 46. Each of fixation mechanisms 46 may be stent-like structures as described above with respect to fixation mechanism 24 of IMD 20.

Fixation mechanism 46A may form ring 48A with lumen 50A. Similarly, fixation mechanism 46B may form ring 48A with lumen 50B. Each of fixation mechanisms 46 may be coupled to opposing sides of housing 44. Fixation mechanism 46A may be structurally anchored to housing 44 using anchoring structure 52A and electrically coupled to telemetry circuitry within housing 44 using connector 54A. Likewise, fixation mechanism 46B may be structurally anchored to housing 44 using anchoring structure 52B and electrically coupled to telemetry circuitry within housing 44 using connector 54B. Anchoring structures 52A and 52B may be formed with respective fixation mechanisms 46 or separately connected to fixation mechanisms 46.

Although housing 44 is coupled to fixation mechanisms 46 on the same side of each of the fixation mechanisms (e.g., at the same circumferential positions), IMD 42 may include different configurations of housing 44 and fixation mechanisms 46. For example, housing 44 may be coupled to one side of fixation mechanism 46A and an opposing side of fixation mechanism 46B (e.g., 180 degrees around ring 48B). This configuration may place housing 44 in approximately the middle of lumens 50A and 50B. In addition, housing 44 may not be placed symmetrically between fixation mechanisms 46. For example, housing 44 may be positioned closer to fixation mechanism 46A than fixation mechanism 46B. Although fixation mechanisms 46 are illustrated as similar sizes, fixation mechanisms 46 may be configured with differing diameters and/or lengths. Differing fixation mechanism dimensions may be used to place IMD 42 in structures having a lumen with differing diameters.

In some examples, fixation mechanisms 46A and 46B may perform different communication functions. For example, fixation mechanism 46A may be configured to receive signals and fixation mechanism 46B may be configured to transmit signals. In other examples, fixation mechanism 46A may be configured to receive and transmit signals and fixation mechanism 46B may be configured to receive signals. These configurations may allow each fixation mechanism to be configured to receive and/or transmit signals with a selected wavelength or frequency. Different implanted or external devices may utilize different signal wavelengths based on transmission distances, energy requirements, or even interference considerations. Alternatively, fixation mechanism 46A may be configured as a radiating portion of an antenna while fixation mechanism 46B may function to position housing 22 within patient 12 without being configured as part of an antenna. Although each of fixation mechanisms 46A and 46B may be separately anchored to housing 44, IMD 42 may be constructed in other configurations. For example, anchoring structures 52A and 52B may be welded, crimped, or otherwise attached to each other within housing 44. If fixation mechanisms 46A and 46B are coupled to separate grounds, each of fixation mechanisms 46A and 46B may be configured to operate with different resonant frequencies. If fixation mechanisms 46A and 46B are coupled to the same ground (e.g., a continuous housing 44) fixation mechanisms 46A and 46B may operate as a single antenna. As a single antenna, connectors 54A and 54B may provide mechanical redundancy.

Figure 5:
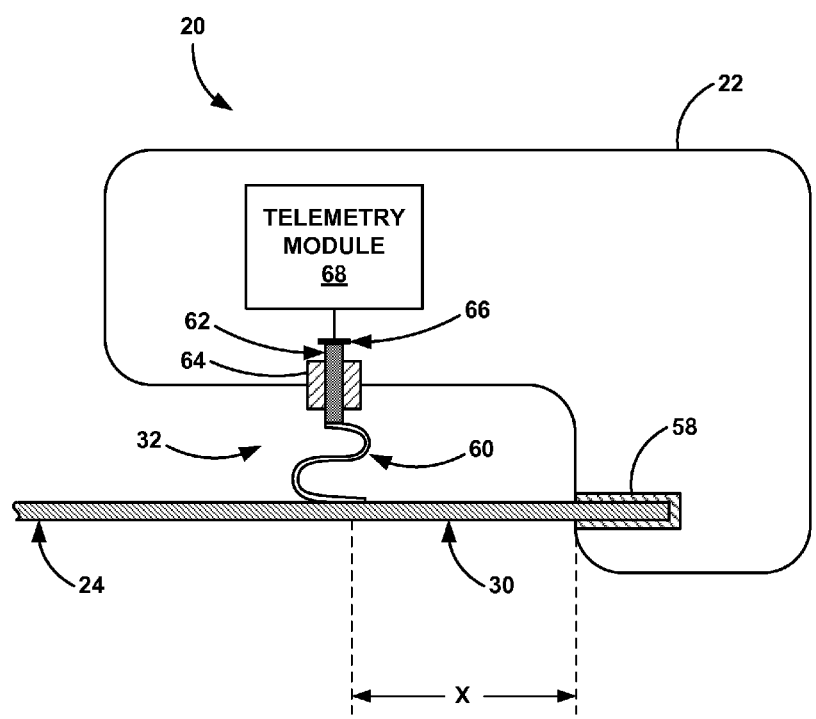
FIG. 5 is a cross-sectional view of an example IMD with a deformable member and a feed-through pin that electrically couple the fixation mechanism to a telemetry module.

FIG. 5 is a cross-sectional view of example IMD 20 with deformable member 60 and feed-through pin 62 that electrically couple fixation mechanism 24 to telemetry module 68. As shown in FIG. 5, IMD 20 includes housing 22 and a proximal portion of fixation mechanism 24. Housing 22 includes anchor slot 58, feed-through slot 64, connector plate 66, and telemetry module 68. Fixation mechanism 24 is structurally anchored to housing 22 using anchoring structure 30.

As shown in FIG. 5, anchoring structure 30 is a portion of fixation mechanism 24 (e.g., anchoring structure 30 is formed of fixation mechanism 24). However, anchoring structure 30 may be a separate member that couples fixation mechanism 24 to housing 22. Anchoring structure 30 may be inserted into anchor slot 58. Anchor slot 58 may have a circular, square, rectangular, ovoid, or an asymmetrical cross-section shaped to accept anchoring structure 30. Anchor slot 58 may be a mechanically reinforced receptacle configured to accept anchoring structure 30. Anchoring structure 30 may be spot welded to anchor slot 58, adhered within anchor slot 58, retained to anchor slot 58 with one or more set screws, or otherwise retained within anchor slot 58. In other examples, anchor slot 58 may be an opening in housing 22 within which anchoring structure 30 is attached to housing 22. Anchor slot 58 may also facilitate the electrical grounding of anchor structure 30 to housing 22. Although anchoring structure 30 may be a relatively straight rod shape, in other examples, anchoring structure 30 may be shaped with an alternative structure that may promote retention and/or reduce rotation within housing 22 such as a bend, curve, notch, or other keyed shape that is inserted into a matched anchor slot 58.

Connector 32 may include both deformable member 60 and feed-through pin 62. Deformable member 60 is electrically and mechanically coupled to fixation mechanism 24. Deformable member 60 may be coupled to fixation mechanism 24 and feed-through pin 62 using spot welding, soldering, crimping electrically conductive adhesive, or other attachment technique. Deformable member 60 may provide strain and/or stress relief to the electrical connection between fixation mechanism 24 and housing 22. Since fixation mechanism 24 may bend and/or twist when implanted in patient 12, a rigid connector 32 may be susceptible to fracture. Therefore, deformable member 60 may allow fixation mechanism 24 to move with respect to housing 22 and reduce the likelihood of connector failure. As shown in FIG. 5, deformable member 60 may be a ribbon connector or other wire-type structure that has extra length when compared to the distance between fixation mechanism 24 and housing 22. In this manner, deformable member 60 may have an arcuate or convoluted shape. This extra length of deformable member 60 may reduce the likelihood that the distance between fixation mechanism 24 and housing 22 would ever become greater than the length of deformable member 60. In an alternative example, deformable member 60 may be a coil or spring that is configured to deform instead of fracture under strain. Other types of deformable members may be used instead. For example, deformable member 60 may be deformable along the axis of deformable member 60 instead of bending radially as found in a ribbon or coil (e.g., deformable member 60 may form a generally straight member between housing 22 and fixation mechanism 24). In other examples, connector 32 may include two or more deformable members in series or in parallel. Although deformable member 60 is shown in FIG. 5 as attached to the end of feed-through pin 62 via a longitudinal length of deformable member 60, deformable member 60 may be attached to feed-through pin 62 using any other attachment technique (e.g., soldering the axial end of deformable member 60 to feed-through pin 62, threading deformable member 60 through a hole or slot in feed-through pin 62, or wrapping deformable member 60 around at least a portion of feed-through pin 62).

Deformable member 60 is also electrically coupled to feed-through pin 62. Feed-through pin 62 passes from the exterior of housing 22 into the interior of housing 222. Feed-through slot 64 may be constructed of an electrically insulated material that electrically isolates feed-through pin 62 from housing 22. Feed-through pin 62 may then contact connector plate 66 to electrically couple feed-through pin 62 to telemetry module 68 (e.g., telemetry circuitry). Connector plate 66 may be constructed as any electrical connection for feed-through pin 62 (e.g., a socket). Feed-through pin 62 may be secured to feed-through slot 64 with an adhesive, friction fit, set screw, or any other technique.

The dimensions of members used for deformable member 60, feed-through pin 62, fixation mechanism 24, and anchoring structure 30 may be selected to achieve a desired impedance and/or radiating surface area of IMD 20. The cross-sectional areas of deformable member 60 and struts of fixation mechanism 24 may be approximately similar. In some examples, deformable member 60 may have a smaller cross-sectional area than the struts of fixation mechanism 24. In other examples, deformable member 60 may have a greater cross-sectional area than the struts of fixation mechanism 24. Additionally, deformable member 60 may have cross-sectional dimensions different than the cross-section of fixation mechanism 24. For example, deformable member 60 may have a wide and thin cross-sectional area (e.g., a ribbon-like structure) while fixation mechanism 24 may have a generally circular cross-sectional area.

In general, deformable member 60 may have a thickness between approximately 0.02 millimeters (mm) and 0.5 mm. In one example, deformable member 60 may have a thickness between approximately 0.20 mm and 0.26 mm. However, deformable member 60 may be constructed of any thickness and/or width appropriate to provide an electrical connection between fixation mechanism 24 and strain relief on the electrical connection.

The distance X between connector 32 and housing 22 may be selected to achieve the proper telemetry with fixation mechanism 24. In other words, distance X may at least partially define the impedance of the antenna that includes fixation mechanism 24. This impedance may thus be selected to match the frequency needed for telemetry between IMD 20 and an external device. In addition, the distance X may be selected to reduce any insertion loss in the antenna. The distance X may be generally defined as the distance along fixation mechanism 24 and/or anchoring structure 30. Thus, distance X may not be measured in a straight line when the member curves or bends between these two points. The endpoints of distance X may be the point that deformable member 60 is attached to fixation mechanism 24 and the external most point at which anchoring structure 30 contacts housing 22.

Generally, the distance X between connector 32 and housing 22 along anchoring structure 30 may be between approximately 1.0 millimeters (mm) and 20.0 mm. In one example, distance X may be between approximately 3.0 mm and 6.0 mm. In another example, distance X may be between approximately 4.0 mm and 5.0 mm. The distance X may be selected based on the equivalent inductance from the shortest circuit including connector 32, anchoring structure 30, and housing 22. The distance X may also be selected based on one or more factors such as materials of fixation mechanism 24 and anchoring structure 30, cross-sectional areas of fixation mechanism 24 and/or anchoring structure 30, surface area of fixation mechanism 24, length of connector 32, surface area of housing 22, and volume of housing 22.

In some examples, the area of housing 22 in which feed-through pin 62 and/or anchoring structure 30 contact housing 22 may be a header portion. The header portion may be formed of a non-conductive, biocompatible material. The header portion may also provide one or more set screws that secure feed-through pin 62 and/or anchoring structure 30 to the header portion and housing 22. In other words, the header portion may be constructed as a distinct portion of housing 22 that is configured to interface with external components (e.g., connector 32 and anchoring structure 30).

As shown in the example of FIG. 5, housing 22 has a rounded "L" shape with connector 32 generally perpendicular to fixation mechanism 24. However, housing 22 may be constructed of any shape such as a cylinder, ovoid, capsule, cube, rectangular cuboid, or any other shape selected to be implanted within patient 12. In addition, connector 32 may not form a generally perpendicular line between fixation mechanism 24 and housing 22. For example, connector 32 may attach to fixation mechanism 24 and/or housing 22 at non-right angles. In other examples, fixation mechanism 24 and/or anchoring structure 30 may not be parallel to the surface of housing 22 at which connector 32 is attached. Although housing 22 is shown with two perpendicular surfaces attaching to connector 32 and anchoring mechanism 30, both of connector 32 and anchoring structure 30 may attach to non-perpendicular surfaces or even a straight surface. According to these and other examples, the attachment, and angles thereof, between connector 32, anchoring structure 30, and housing 22 may differ from that of the example of FIG. 5.

Figure 6:
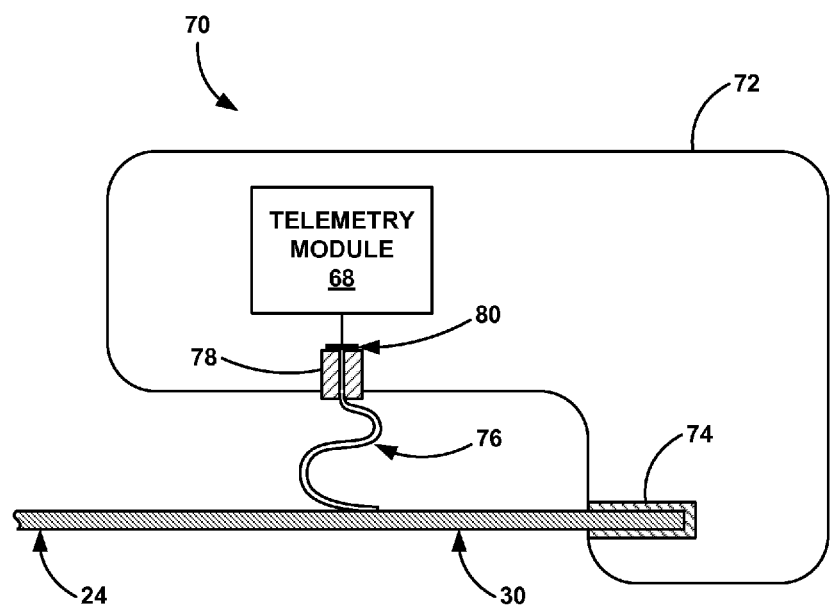
FIG. 6 is a cross-sectional view of an example IMD with a deformable member that feeds through the housing to electrically couple the fixation mechanism to a telemetry module.

FIG. 6 is a cross-sectional view of example IMD 70 with deformable member 76 that feeds through housing 22 to electrically couple fixation mechanism 24 to telemetry module 68. IMD 70 is a similar to IMD 20 illustrated in FIG. 5, but IMD 70 does not include a separate feed-through pin for the connector. As shown in FIG. 6, IMD 70 includes housing 72 and a proximal portion of fixation mechanism 24. Housing 72 includes anchor slot 74, feed-through slot 78, connector plate 80, and telemetry module 68. Fixation mechanism 24 is structurally anchored to housing 72 using anchoring structure 30.

Deformable member 76 may be the connector that electrically couples fixation mechanism 24 to telemetry module 68. Instead of utilizing a feed-through pin to pass the electrical signal through housing 72, deformable member 76 is attached directly within feed-though slot 78. Deformable member 76 may be coupled to fixation mechanism 24 using spot welding, soldering, crimping, electrically conductive adhesive, or other attachment technique. Deformable member 76 may also be attached within feed-through slot 78 using spot welding, soldering, an adhesive, or other attachment technique. Feed-through slot 78 may be electrically insulated from housing 72 such that deformable member 76 does not make electrical contact with housing 72. However, deformable member 76 may be electrically coupled to telemetry module 68 via contact 80. In some examples, deformable member 76 may be attached to contact 80.

By constructing IMD 70 such that deformable member 76 passes through housing 72 to connect with telemetry module 68, IMD 70 may limit the number of physical connections between fixation mechanism 24 and telemetry module 68 that may be subject to fracture or separation over time. In other words, a single segment of deformable member 76 may more structurally durable as deformable member 76 is deformed when implanted within patient 12. In this manner, deformable member 76 may provide strain and/or stress relief to the electrical connection between fixation mechanism 24 and housing 72 without a separate feed-through pin (e.g., feed-through pin 62 of FIG. 5). Deformable member 72 may thus allow fixation mechanism 24 to move with respect to housing 72 and reduce the likelihood of connector failure.

Deformable member 76 may be a ribbon connector that has extra length when compared to the distance between fixation mechanism 24 and housing 72. In an alternative example, deformable member 76 may be a coil or spring that is configured to deform instead of fracture under strain. Other types of deformable members may be used instead. For example, deformable member 50 may be axially deformable instead of radially deformable as found in a ribbon or coil. Alternatively, deformable member 76 may have varying cross-sectional dimensions along the length of deformable member 76. For example, deformable member 76 may be a ribbon-like shape distal of housing 22 and a circular shape that is disposed within feed-through slot 78. Deformable member 76 may be molded, cast, stamped, or extruded from an electrically conductive material to form the selected dimensions for IMD 70. In some examples, deformable member 76 may include an electrically insulative coating (e.g., a bio-compatible polymer) to protect deformable member 76 and adjacent cellular activity within patient 12.

Figure 7:
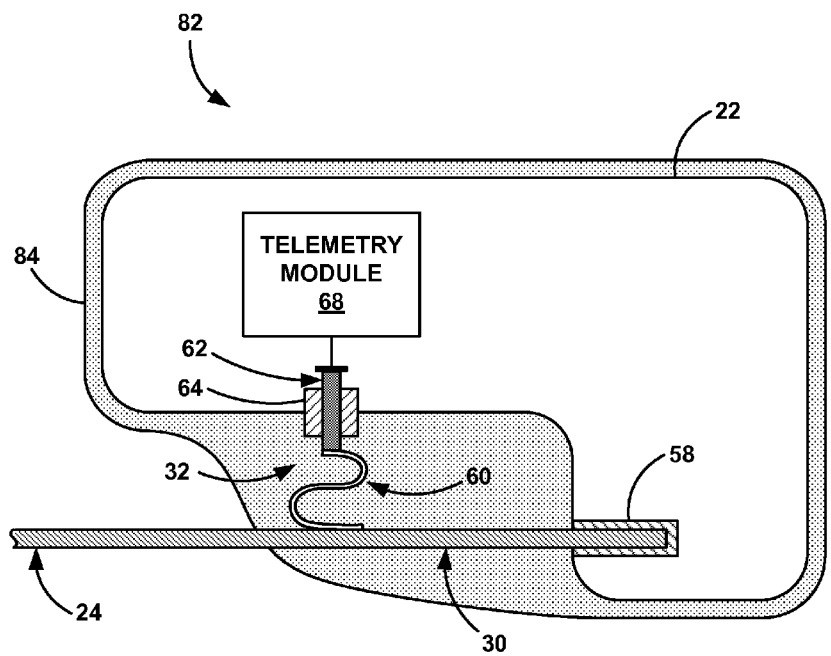
FIG. 7 is a cross-sectional view of an IMD that includes an overmold that encompasses a deformable member and a feed-through pin.

FIG. 7 is a cross-sectional view of IMD 82 that includes overmold 84. IMD 82 may be substantially similar to IMD 20 of FIG. 5. However, IMD 82 may also include overmold 84 that generally surrounds housing 22 and other components of IMD 82. Overmold 84 may be constructed of a biocompatible polymer that is moldable around housing 22. Overmold 84 may be a thermoplastic elastomer or other polymer suitable for forming around housing 22 and deformable member 60. Example polymers used to construct overmold 84 may be polyethylene, polypropylene, polyvinyl chloride, fluoroplastics, polycarbonate, polypropylene, polyurethane, or any other similar polymers.

Overmold 84 may be constructed to encase the connector, e.g., connector 32 that includes deformable member 60 and feed-through pin 62 or deformable member 76. Overmold 84 may completely surround deformable member 60 to protect the deformable member from stresses and strains when implanted within patient 12. As shown in FIG. 7, overmold 84 may also enclose anchoring structure 30. In this manner, only fixation mechanism 24 may exit out of overmold 84. In other examples, overmold 84 may only enclose a portion of housing 22 (e.g., overmold 84 may enclose one side of IMD 20). In one example, overmold 84 may only enclose a portion of deformable member 60, a portion of fixation mechanism 24, and/or a portion of anchoring structure 30. Overmold 84 may be configured to encase as much or as little of IMD 82 such that IMD 82 is compatible with patient 12 and overmold 84 may protect delicate components, e.g., deformable member 60 and feed-through pin 62.

Figure 8A:
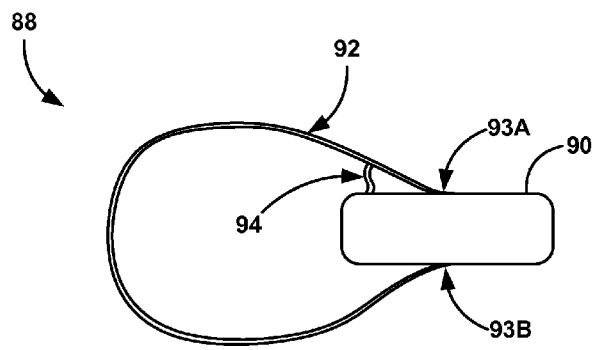
FIGS. 8A and 8B are conceptual diagrams illustrating example IMDs with various fixation mechanisms that function as radiating and receiving elements of an antenna.
Figure 8B:
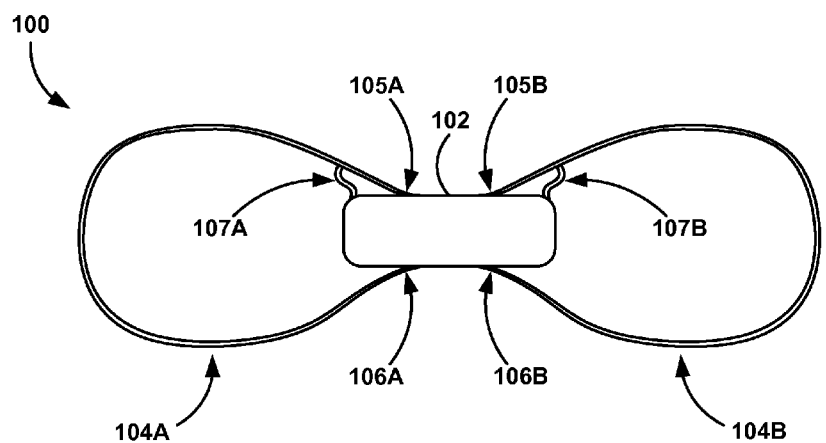

FIGS. 8A and 8B are conceptual diagrams illustrating example IMDs 88 and 100 with various fixation mechanisms that function as radiating elements of an antenna for the respective IMDs. IMDs 88 and 110 may be similar to IMD 20 of FIG. 5. However, IMDs 88 and 110 may utilize different shaped fixation mechanisms than that of IMD 20. As shown in FIG. 8A, IMD 88 includes housing 90 and fixation mechanism 92. Fixation mechanism 92 is a loop that may be used to position IMD 88 within the vasculature or other anatomical area of patient 12. Fixation mechanism 92 is attached to housing 90 at anchoring locations 93A and 93B. In this manner, fixation mechanism 92 includes a fixation loop that is mechanically coupled to housing 90.

Although fixation mechanism 92 may include the anchoring structures that structurally attach fixation mechanism 92 to housing 90, separate anchoring structures may be used in other examples to couple fixation mechanism 92 to housing 90. Fixation mechanism 92 may be electrically grounded to housing 90 at one or both of anchoring locations 93A and 93B. In other examples, anchoring locations 93A and 93B may be located at any position on the surface of housing 90.

Connector 94 may electrically couple fixation mechanism 92 to telemetry circuitry within housing 90. Connector 94 may be located a pre-selected distance along fixation mechanism 92 from anchoring location 93A. Connector 94 may also be insulated such that a conductive wire is encased by an electrically insulative material. In addition, connector 94 may include a deformable member, and in some examples, a feed-through pin that passes the electrical signal from connector 94 though housing 90 to the telemetry circuitry. For example, connector 94 may be coupled to a telemetry module using similar techniques as described above with respect to connector 32 and deformable member 76. Although housing 90 is shown as a capsule shape, housing 90 may be configured into any shape selected for implantation within patient 12.

As shown in FIG. 8B, IMD 100 includes multiple fixation mechanisms 104A and 104B. Fixation mechanisms 104A and 104B are loops that may be used to position IMD 100 within the vasculature or other anatomical area of patient 12. Fixation mechanism 104A is attached to housing 102 at anchoring locations 105A and 106A. Fixation mechanism 104B is attached to housing 102 at anchoring locations 105B and 106B. In this manner, fixation mechanisms 104A and 104B each include a fixation loop that is mechanically coupled to housing 102. Although fixation mechanisms 104A and 104B may include the anchoring structures that structurally attach fixation mechanisms 104A and 104B to housing 102, separate anchoring structures may be used in other examples to couple fixation mechanisms 104A and 104B to housing 102. Each of fixation mechanisms 104A and 104B may be electrically grounded to housing 102 at one or both of respective anchoring locations 105A or 106A and 105B or 106B. In other examples, anchoring locations 105A, 106A, 105B, or 106B may be located at any position on the surface of housing 102.

Fixation mechanisms 104A and 104B are shown as approximately the same size in FIG. 8B. However, fixation mechanisms 104A and 104B may be loops of different sizes and/or structures of different shapes. The number of fixation mechanisms in IMD 100 may vary. In other examples, IMD 100 may include more than two fixation mechanisms 104A and 104B. For example, IMD 100 may include four fixation mechanisms distributed around the perimeter of housing 102. Multiple fixation mechanisms, such as the loops of IMD 100, may be separate from each other. Alternatively, each of the fixation mechanisms may overlap one or more other fixation mechanism. For example, two loops may be attached to housing 102 such that the planes of each loop intersect with one another. These different configurations of fixation mechanisms may be selected for specific locations within patient anatomy and/or to achieve a desired radiating portion of the antenna of IMD 102.

Figure 9:
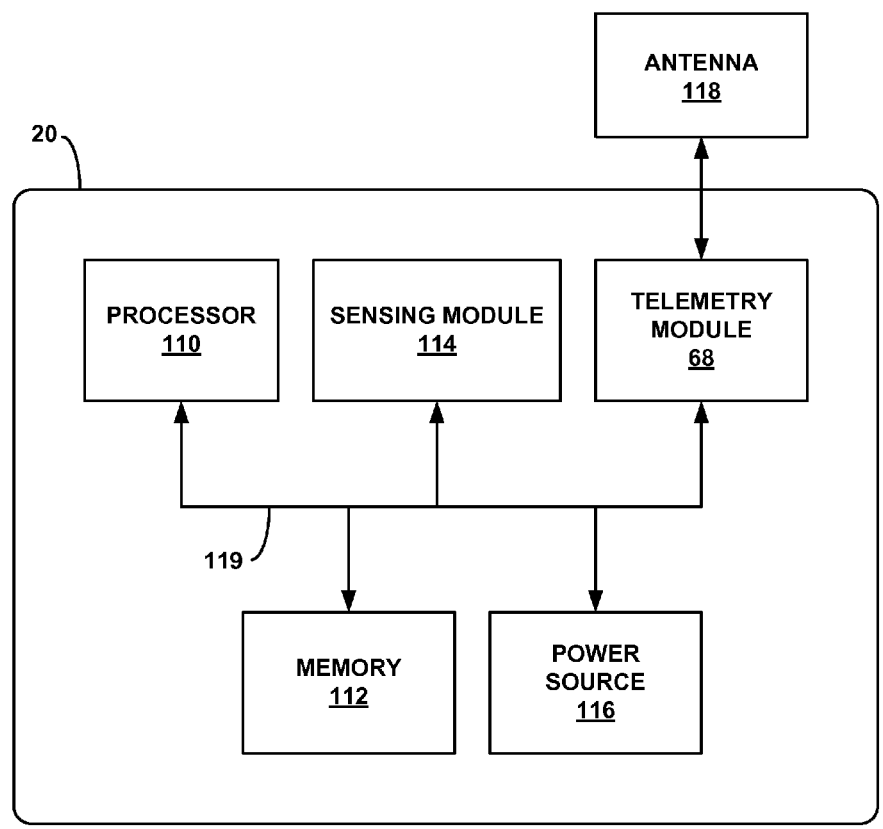
FIG. 9 is a block diagram illustrating components of an IMD.

FIG. 9 is a block diagram illustrating components of IMD 20. The components described with respect to IMD 20 may also be used within any other IMD, such as IMD 14, 42, 70, 82, 88, and 100. IMD 20 may include processor 110, memory 112, sensing module 114, power source 116, antenna 118, and telemetry module 68. The components of IMD 20 are shown to be interconnected by a data/communication bus 119, but may be interconnected by other means including direct electrical or non-electrical connections or a combination of different types of connections.

As described above, IMD 20 may sense one or more parameters (e.g., physiological or biological parameters) of patient 12 and/or detect one or more conditions from the sensed parameters. As described herein, sensing module 114 may be configured to obtain signals related to one or more parameters of patient 12. For example, sensing module 114 may be a pressure sensing module that detects the pressure of the surrounding environment within which IMD 20 is placed. In other examples, IMD 20 may include other types of sensors instead of or in addition to a pressure sensing device, such as pH sensor, oxygen sensor, temperature sensor, electrodes, or any other type of sensor.

The parameters sensed by sensing module 114 may be stored in memory 112. In some instances, the sensed parameters may be stored in raw form. In other instances, the sensed parameters may be processed and the processed parameters may be stored in memory 112. For example, IMD 20 may include one or more analog or digital components that amplify and filter the sensed parameters and store the filtered parameters in memory 112. The parameters stored in memory 112 may, in some cases, be retrieved and further processed by processor 110. Processor 110 may, for example, process the sensed parameters to monitor or detect a condition of patient 12.

Processor 110 controls telemetry module 68 to transmit communications to and/or receive communications from another device, such as a body worn device, external device 18, or another implanted medical device. As such, telemetry module 68 may include one or more transceivers or, in instances in which IMD 20 only supports unidirectional communication, one or more transmitters or one or more receivers. In some instances, telemetry module 68 may include two or more sets of components, e.g., one for inductive communication and one for RF communication. As described in detail above, antenna 118 may include at least a portion of fixation mechanism 24, connector 32, and in some examples, anchoring structure 30.

Processor 110 may provide the data to be transmitted and control signals for transmit and receive circuitry within telemetry module 68, e.g., via data bus 119 Telemetry module 68 transmits the data to another device (e.g., a body worn device, external device 18, or another implanted device) in accordance with the control signals from processor 110. Telemetry module 68 may also provide data received from another device to processor 110 in the case of incoming communications. Processor 110 may analyze the received data, store the received data within memory 112 and configure components of IMD 20 in accordance with the received data.

Telemetry module 68 (e.g., telemetry circuitry) includes any suitable hardware, firmware, software or any combination thereof for communicating with another device. For example, telemetry module 68 may include appropriate modulation, demodulation, frequency conversion, filtering, amplifier or other components for transmission and reception of data. Telemetry module 68 is also coupled to an antenna 118, such as any of the antenna configurations described herein, for transmitting and receiving signals. Antenna 118 may include multiple components such as fixation mechanisms 24, 46A, 46B, 92, 104A, and/or 104B.

Power source 116 may include a rechargeable or non-rechargeable battery. A non-rechargeable battery may be selected to last for several years, while a rechargeable battery may be charged from an external charging device on an as-need basis, e.g., daily or weekly basis. In either case, and especially in the case of the non-rechargeable battery, the amount of power of the battery is limited. As such, it is desirable to reduce the amount of power drained from power source 116 as much as possible.

IMD 20 of FIG. 9 is provided for purposes of illustration. IMD 20 may include more or fewer components than those illustrated in FIG. 9. For example, IMD 20 may be an implantable medical device configured to also provide therapy, such as electrical stimulation therapy or drug delivery therapy, in accordance with parameters of one or more selected therapy programs. In this case, IMD 20 may include a therapy module (not shown) to generate therapy according to one or more therapy programs and deliver the therapy to patient 12. Example therapies may include cardiac pacing, acoustic stimulation or other hearing therapy, or drug delivery therapy. In the case of electrical stimulation therapy, the therapy module may include a stimulation generator that generates and delivers electrical stimulation therapy, e.g., in the form of pulses or shocks, via one or more electrodes on housing 22, a header or a lead extending from IMD 20. Processor 110 may control the stimulation generator to deliver electrical stimulation pulses with amplitudes, pulse widths, frequency, and/or electrode polarities specified by the one or more therapy programs. In the case of drug delivery therapy, the therapy module may include a pump that delivers a drug or therapeutic agent, e.g., via a catheter or other delivery mechanism. Processor 110 may control the pump to deliver the drug or therapeutic agent with the dosage and frequency (or rate) specified by the one or more therapy programs. As such, the techniques of this disclosure should not be considered limited to the example described in FIG. 9.

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These examples, however, should not be considered limiting of the techniques described in this disclosure. For instance, the techniques of this disclosure may be used with any fixation mechanism for which a sufficient signal may be radiated to and from another device. Moreover, the techniques may further be applicable beyond the use of a fixation mechanism. Any suitable radiating structure may be connected to the housing an electrical connector to electrically couple the radiating structure to telemetry circuitry and a separate anchoring structure to structurally attach the radiating structure to the housing. These and other examples are within the scope of the following claims.

What is claimed is:

1. An implantable medical device comprising:
   an implantable housing comprising a telemetry module;
   a fixation mechanism comprising an anchoring structure configured to mechanically anchor the fixation mechanism to the implantable housing, wherein the anchoring structure is configured to electrically ground the fixation mechanism to the implantable housing; and
   a connector electrically connecting the fixation mechanism to the telemetry module, wherein the fixation mechanism is configured to operate as at least a portion of an antenna to at least one of transmit or receive communication signals, and wherein the anchoring structure, instead of the connector, is configured to provide structural support between the fixation mechanism and the implantable housing.

2. The device of claim 1, wherein a distance between the connector and the housing along the anchoring structure is between approximately 3.0 millimeters (mm) and 6.0 mm, and wherein the distance at least partially defines the impedance of the antenna.

3. The device of claim 1, wherein the connector comprises:
   an electrically conductive deformable member connected to the fixation mechanism and configured to allow at least a portion of the fixation mechanism to move with respect to the housing; and
   a feed-through pin electrically coupling the deformable member to the telemetry module, wherein the feed-through pin is electrically isolated from the housing.

4. The device of claim 1, wherein the connector is a deformable member configured to allow the fixation mechanism to move with respect to the housing and electrically isolated from the housing.

5. The device of claim 1, wherein the connector is a portion of the fixation mechanism.

6. The device of claim 1, further comprising an overmold that encases the connector and at least a portion of the housing.

7. The device of claim 1, wherein the fixation mechanism is a cylindrical stent-like structure that is configured to lodge against a vessel wall.

8. The device of claim 1, wherein the fixation mechanism is mechanically anchored in a single location of the housing.

9. The device of claim 1, wherein the fixation mechanism is mechanically anchored in at least two different locations of the housing.

10. The device of claim 1, further comprising a sensor within the housing and configured measure one or more parameters.

11. The device of claim 1, further comprising a therapy module within the housing and configured to deliver therapy to a patient.

12. The implantable medical device of claim 1, wherein the antenna comprises a planar inverted F-antenna resonant at a quarter-wavelength of a transmission signal.

13. A device comprising:
    a housing configured to be implanted within a patient;
    a fixation mechanism configured to be implanted within the patient;
    an anchoring structure configured to mechanically anchor the fixation mechanism to the housing, wherein the anchoring structure is configured to electrically ground the fixation mechanism to the housing; and
    a connector configured to electrically couple the fixation mechanism to telemetry circuitry within the housing, wherein the anchoring structure, instead of the connector, is configured to provide structural support between the fixation mechanism and the housing.

14. The device of claim 13, wherein the connector is configured to transfer excitation energy between the telemetry circuitry and the fixation mechanism, and wherein the fixation mechanism is configured to operate as at least a portion of an antenna to at least one of transmit or receive communication signals.

15. The device of claim 13, wherein
the connector is an electrically conductive deformable member configured to allow the fixation mechanism to move with respect to the housing and to be electrically isolated from the housing.

16. The device of claim 13, wherein the fixation mechanism is a cylindrical stent-like structure that is configured to lodge against a vessel wall within the patient.

17. The device of claim 13, wherein the fixation mechanism, the anchoring structure, and the connector are formed of a single structure.

18. The device of claim 13, wherein the housing comprises a sensor configured to measure one or more parameters associated with the patient.

19. The device of claim 13, wherein the device is configured to communicate with an external programmer via the fixation mechanism, the external programmer configured to program the device.

20. The device of claim 13, wherein the device is a first device, and wherein the first device is configured to communicate with a second device configured to be implanted within the patient.

21. The device of claim 20, wherein the first device is configured to relay data between the second device and an external programmer.

22. The device of claim 13, wherein the fixation mechanism is configured to operate as at least a portion of a planar inverted F-antenna resonant at a quarter-wavelength of a transmission signal.

23. A device comprising:
an implantable housing comprising a telemetry module;
means for attaching the housing to an anatomical structure within a patient, wherein the attaching means is mechanically anchored to the implantable housing, and wherein the attaching means comprises means for electrically grounding the attaching means to the implantable housing; and
means for electrically connecting the attaching means to the telemetry module, wherein the attaching means is configured to operate as at least a portion of an antenna to at least one of transmit or receive communication signals, and wherein the electrically grounding means, instead of the electrically connecting means, comprises means for providing structural support between the attaching means and the implantable housing.

24. The device of claim 23, wherein the electrically connecting means comprises means for allowing the attaching means to move with respect to the housing, and wherein the housing comprises means for electrically isolating the electrically connecting means from the housing.

25. The device of claim 23, further comprising means for measuring one or more parameters associated with the patient.

26. The device of claim 23, wherein the antenna comprises a planar inverted F-antenna resonant at a quarter-wavelength of a transmission signal.

* * * * *